US012741083B2

(12) United States Patent
Chatterjee et al.

(10) Patent No.: US 12,741,083 B2
(45) Date of Patent: Sep. 22, 2026

(54) MACHINE AND ACCESSORIES FOR PERFORMING DOUBLE VOLUME EXCHANGE TRANSFUSION IN NEONATES

(71) Applicant: COUNCIL OF SCIENTIFIC AND INDUSTRIAL RESEARCH, New Delhi (IN)

(72) Inventors: Arindam Chatterjee, Chandigarh (IN); Sanjeev Verma, Chandigarh (IN); Sourabh Dutta, Chandigarh (IN); Dinesh Pankaj, Chandigarh (IN); Gurinderjit Singh, Chandigarh (IN); Sarbjeet Singh, Chandigarh (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 428 days.

(21) Appl. No.: 18/560,059

(22) PCT Filed: Mar. 4, 2022

(86) PCT No.: PCT/IN2022/050195
§ 371 (c)(1),
(2) Date: Nov. 9, 2023

(87) PCT Pub. No.: WO2022/239018
PCT Pub. Date: Nov. 17, 2022

(65) Prior Publication Data

US 2024/0238511 A1 Jul. 18, 2024

(30) Foreign Application Priority Data

May 9, 2021 (IN) ............................ 202111020979

(51) Int. Cl.
*A61M 5/142* (2006.01)
*A61M 5/14* (2006.01)
(Continued)

(52) U.S. Cl.
CPC ........ *A61M 5/1422* (2013.01); *A61M 5/1458* (2013.01); *A61M 5/16859* (2013.01);
(Continued)

(58) Field of Classification Search
CPC ............ A61M 5/1422; A61M 5/14216; A61M 5/1458; A61M 5/16859; A61M 5/16881;
(Continued)

(56) References Cited

U.S. PATENT DOCUMENTS 3,990,444 A 11/1976 Vial
4,457,747 A 7/1984 Tu
(Continued)

FOREIGN PATENT DOCUMENTS

CN 1625418 A 6/2005
CN 112717218 A 4/2021
(Continued)

OTHER PUBLICATIONS

International Search Report and Written Opinion received in International Application No. PCT/IN2022/050195, mailed on Jun. 21, 2022.

*Primary Examiner* — Katrina M Stransky
(74) *Attorney, Agent, or Firm* — Knobbe, Martens, Olson & Bear, LLP

(57) ABSTRACT

A DVET unit is disclosed that comprises a first syringe and a second syringe having a first plunger and a second plunger, adapted to execute a backward stroke and a forward stroke in the respective syringe. The DVET unit also includes a first valve and a second valve. Further, the first valve is closed and the second valve is opened to draw blood from the source and the specimen into the first syringe and the second syringe. Moreover, the first valve is opened and the second valve is closed to pump the blood, drawn during the back-
(Continued)

ward stroke, from the first syringe and the second syringe into the specimen and the waste bin.

9 Claims, 6 Drawing Sheets

(51) Int. Cl.
*A61M 5/145* (2006.01)
*A61M 5/168* (2006.01)

(52) U.S. Cl.
CPC . *A61M 5/16881* (2013.01); *A61M 2005/1401* (2013.01); *A61M 2005/14208* (2013.01); *A61M 2005/16868* (2013.01); *A61M 2202/0007* (2013.01); *A61M 2202/0014* (2013.01); *A61M 2202/0413* (2013.01); *A61M 2205/106* (2013.01); *A61M 2205/128* (2013.01); *A61M 2205/15* (2013.01); *A61M 2205/18* (2013.01); *A61M 2205/3306* (2013.01); *A61M 2205/3331* (2013.01); *A61M 2205/502* (2013.01); *A61M 2210/1466* (2013.01); *A61M 2240/00* (2013.01)

(58) Field of Classification Search
CPC ........... A61M 2005/1401; A61M 2005/14208; A61M 2005/16868; A61M 5/14; A61M 39/22; A61M 1/02; A61M 1/67
See application file for complete search history.

(56) References Cited

U.S. PATENT DOCUMENTS

| | | | | |
|---|---|---|---|---|
| 4,457,751 | A | 7/1984 | Rodler | |
| 5,256,157 | A | 10/1993 | Samiotes et al. | |
| 5,547,470 | A | 8/1996 | Johnson et al. | |
| 6,106,509 | A | 8/2000 | Loubser | |
| 7,083,587 | B2 | 8/2006 | Chattopadhyay et al. | |
| 10,543,306 | B2 | 1/2020 | Brieske | |
| 2003/0181841 | A1* | 9/2003 | Chattopadhyay ....... | A61M 1/67 604/7 |
| 2017/0281857 | A1* | 10/2017 | Wight ................. | A61M 5/1452 |

FOREIGN PATENT DOCUMENTS

| | | | | |
|---|---|---|---|---|
| EP | 1634613 | A1 * | 3/2006 | .......... A61M 5/1422 |
| EP | 2190499 | A1 | 2/2010 | |

* cited by examiner

600

Put power adapter to (134) and press (136) to power on

Check if (104) & (106) are fixed between (128) & (176)

No

Set (106) & (106) in proper place

Yes

Check if "*" key of (170) is pressed?

No

Yes

Press "RESET" key of (170) to reset all the parameters entered previously

Set the value of the following parameters displayed in (172) through (170)
1) VOLUME/STROKE
2) DURATION OF STROKE
3) TOTAL EXCHANGE VOLUME Check if parameters entered through (170) are correct No Re-enter the values by pressing "DELETE", "FRWD" & "BACK" buttons of (170)

Yes

Calculate Total Number of Cycle = (Total Exchange volume/Volume per stroke)

Calculate "Total Step Count" for stepper motor (124) for clockwise movement

Initialize "Current_Cycle = 0" && "Step_Count = 0"

Check if "START" key of (170) is pressed?

No

Yes

Open valve (110) and Close valve (108)

Turn on Red LED (172B) to begin the process

Start clockwise rotation of stepper motor (124) to extract the infected blood through umbilical vein (102A) of neonate (102) through the (112) (150E) (110) (116) (150F) to (106) and Fresh blood from (142) through the path (150A) (118) (114) to (104)

Step Count_1 = (Step Count + 1);
Step Count = Step Count_1;

Check if "PAUSE" key of (170) is pressed?

No

Yes

Stop the stepper motor (124)

Check if "PAUSE" key of (170) is pressed again?

No

Yes

Check if air-bubble/clot is detected by (160)?

No

Yes

Blow Buzzer (412) and stop (124)

Check if "BUBBLE" key of (170) is pressed

No

Yes

Check if a pressure variation is detected by (162)

No

Yes

Blow Buzzer (412) and stop (124)

Check if "PRESSURE" key of (170) is pressed

No

Yes

Check if Step_Count = Total Step_Count?

No

Yes

Delay 5 Seconds

Close valve (110) and Open valve (108)

Initialize "Step Count = 0"

Calculate "Total Step Count" for stepper motor (124) for anti-clockwise movement Start anti-clockwise rotation of stepper motor (124) to push the fresh blood through umbilical vein (102A) of neonate (102) through the path (150C), (108), (150D), (112) and infected blood through the path (150F) (116) (150G) (120) (150H) to (144)

Step Count_2 = (Step Count + 1);
Step Count = Step Count_2;

Check if "PAUSE" key of (170) is pressed?

No

Yes

Stop the stepper motor (124)

Check if "PAUSE" key of (170) is pressed again?

No

Yes

Check if air-bubble/clot is detected by (160)?

No

Yes

Blow Buzzer (412) and stop (124)

Check if "BUBBLE" key of (170) is pressed?

No

Yes

Check if a pressure variation is detected by the combination of (162)

No

Yes

Blow Buzzer (412) and stop (124)

Check if "PRESSURE" key of (170) is pressed?

No

Yes

Check if Step_Count = Total Step_Count ?

No

Yes

Check if Total Number of Cycle = Current_Cycle?

No

Current_Cycle = Current_Cycle +1;
Step_Count = 0

Delay 5 Seconds

Blow Buzzer (412) for 1 second to indicate completion of a single cycle

Yes

Turn on Green LED (172A) and turn off Red LED (172B) to indicate the completion of process Blow Buzzer (412) for 5 second to indicate completion of the process Process Completed (Stop)

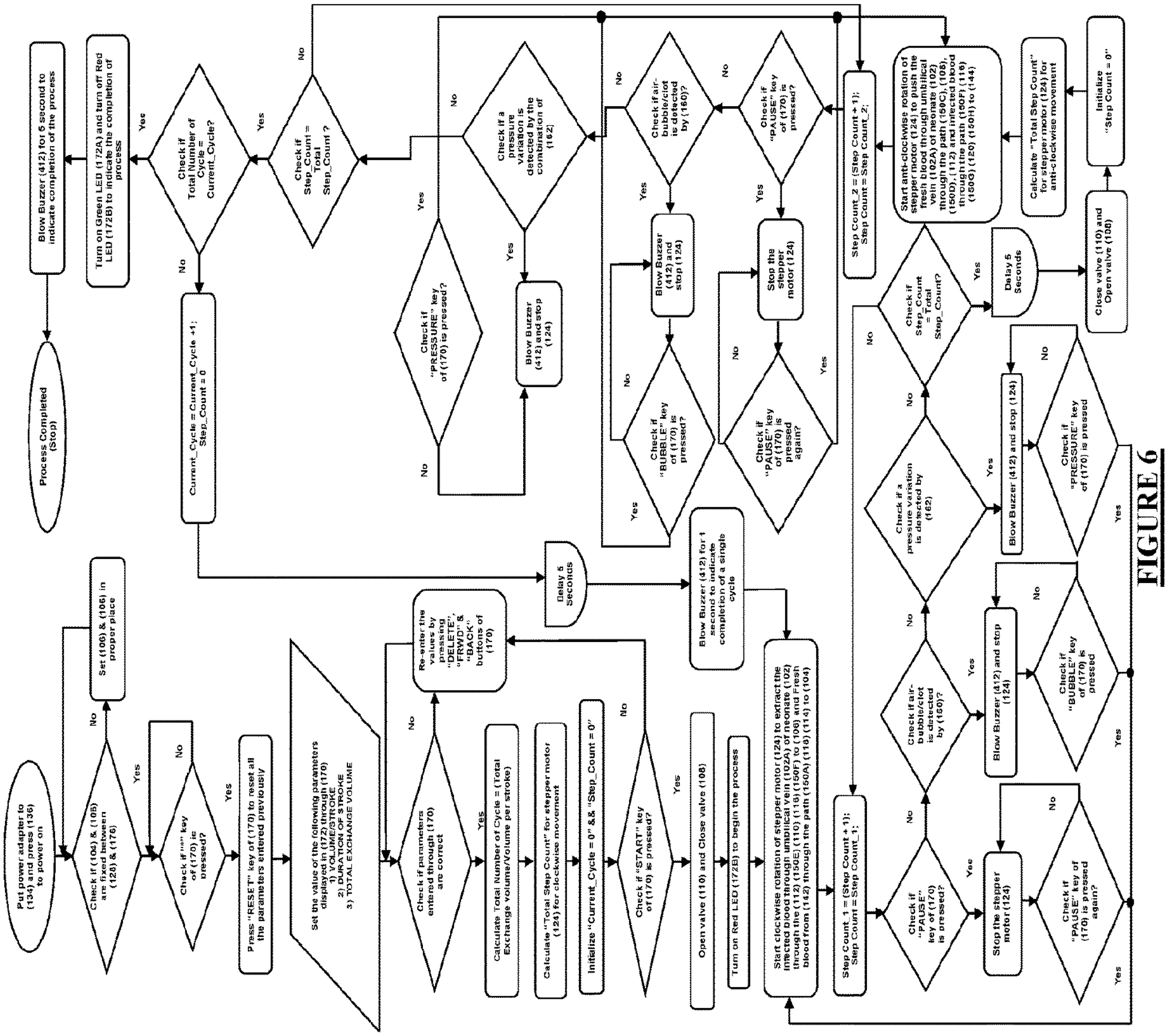

FIGURE 6

MACHINE AND ACCESSORIES FOR PERFORMING DOUBLE VOLUME EXCHANGE TRANSFUSION IN NEONATES

FIELD OF THE INVENTION

The present disclosure relates to a device for blood transfusion in neonates process through umbilical route of neonates.

BACKGROUND

Severe jaundice (hyperbilirubinemia) is a common problem amongst newborn infants. Most infants with severe jaundice require only phototherapy but a few do not respond to phototherapy and end up requiring a double volume exchange transfusion (DVET).

DVET involves replacing the entire blood volume of the neonate twice over with adult donor blood. In each cycle, the amount of neonatal blood that is removed is replaced by an equivalent volume of donor blood. These cycles go on in the same sequence until a total blood volume equal to twice the calculated neonatal blood volume is removed and an equivalent amount replaced. Since the average blood volume of a neonate is 80-100 ml/kg, the usual DVET procedure goes on for about an hour to an hour-and-a half and involves approximately 40 to 50 cycles. Presently, the blood DVET are done manually through the circuit comprising of disposable 3-way valves and syringe arrangement, maintain a fixed flow rate of infusion and extraction, keeping a manual record of each cycle, total number of cycles and sensing of air bubble/blood clot through naked eyes. All these cumbersome processes occupy doctor's and his/her assistant's precious time and energy. There is a high risk of errors occurring with the current manual process. These errors include missing phases of a cycle, missing an entire cycle, incorrect volume of blood withdrawn or infused, accidental infusion of air bubbles or clots, that could potentially cause embolism.

Various devices are known to perform DVET. One of the devices is disclosed in a U.S. Pat. No. 3,990,444 dated Nov. 9, 1976: BLOOD TRANSFUSION APPARATUS which relates a device for drop by drop regulation and control of blood flow rate using roller type mechanical pump. The volume is controlled by detecting the falling drop. There are various drawbacks of such a device, such as the pump is unidirectional and it cannot be used to draw the blood out from the patient. Moreover, there is no detection of high/low pressure to detect the kinking and leakages in the fluid flow line. In addition, there is no GUI and keyboard to display the parameters.

Another device is disclosed in a U.S. Pat. No. 4,457,747 dated Jul. 3, 1984; EXCHANGE TRANSFUSION MACHINE which relates to an exchange transfusion device with two coupled, automatically driven syringes, one in a blood withdrawal system and one in a fresh blood injection system. The system uses 4 syringes, 4 stop-corks valves and 2 pricks in the body. The syringes in the withdrawal and injection phase of an exchange transfusion are driven at a slow steady rate, but on the refill and discard phase are driven at a high rate to avoid clotting of standing blood in the withdrawal and injection systems. The drawbacks of such a system is that the use of two pricks point is painful and the use of 4 syringes and 4 stop-corks valves is not a major advancement over the manual system. Moreover, multiplicity of syringes and stop-cock valves increases chances of nosocomial infections, blockages, leakages, and sources of air and clots that can embolize.

Yet another device is disclosed in a U.S. Pat. No. 4,457,751 dated Jul. 3, 1984; AUTOMATIC INFUSON PUMP which relates to an exchange transfusion device for the intravenous or intra-arterial infusion of liquid medicine consists of frequency generator for operating the infusion pump motor to vary the infused dosage step-by-step after an adjustable time delay by changing the frequency in dependence on physical parameters taken from the patient body, and suddenly rising or falling changes in the physical parameters, cause the device to be turned off by raising an alarm. The drawbacks of such a system are that the syringe movement is unidirectional and such a system is designed for infusion of liquid medicine rather than performing DVET in neonates. Moreover, the electronic components used in such a system are bulky and consumed more power as compared to currently available systems.

Yet another device is disclosed in a U.S. Pat. No. 5,256,157 dated Oct. 26, 1993; AUTOMATED INFUSION PUMP WITH REPLACEABLE MEMORY CARTRIDGES which is related to a drug infusion pump of replaceable memory cartridges (EEPROM) system for dispensing a drug to a patient in accordance with a predetermined therapeutic modality. The system has a drug delivering member controlled by a microprocessor and replaceable memory cartridges with variable dosage scheme. As per the requirement of patient and clinicians the required dosage scheme is burn on the memory cartridges (EEPROM) and insert to the machine, before operation. The drawbacks of such a system are that the syringe movement is unidirectional and the device designed for drug infusion rather than performing DVET in neonates. Moreover, the device does not have alarm for air-bubble/clot and pressure detection.

Yet another device is disclosed in a U.S. Pat. No. 5,547,470 dated Aug. 20, 1996; AUTOMATED DRUG INFUSION SYSTEM which relates to a control system for use with an automated intravenous drug and fluid infusion system having four channels, three for drugs and one for fluid infusion. Each channel works independently and operated through a microprocessor. Before infusion the drugs are identified by a bar code reader. Floppy disc is used for data storage (patient case information, event history, drug usage etc.). The draw backs of this system is that it detects air bubble/clot at the beginning of the process, but not responsive if bubble/clot arises in between any time during the process. Moreover, the syringe movement is unidirectional and the system is used for drug transfusion only, not blood.

Yet another device is disclosed in a U.S. Pat. No. 6,106,509 dated Aug. 22, 2000; CLOSED CIRCUIT AUTOLOGOUS SEQUEST RATION RESERVOIR SYSTEM which relates to an apparatus for autologous sequestration of blood from a patient to the oxygenated blood bags kept in contact with the patient throughout the surgery. This blood is collected in bags during surgery and is trickled back into patient's system using manual valves and pump thereby assuming continuity with the patient's circulation system. The drawbacks of such a system that the blood is not extracted in a controlled way and the system does not have safety alarms for bubble/clot and pressure and cannot be used for performing DVET.

Yet another device is disclosed is a U.S. Pat. No. 7,083,587 B2 dated Aug. 1, 2006: BLOOD TRANSFUSION SYSTEM which relates to a blood transfusion system set up consisting of Y-Shaped connector, one-way valves and two syringes. At the time of suction, the blood is taken out from the patient body through one syringe and simultaneously the other syringe is filled up with fresh blood. During infusion the patient infected blood is sent to the waste, while the fresh blood is infused to the patient. The draw backs includes that due to the one way valves the infected blood gets mixed up with the fresh blood, thereby decreasing the transfusion efficiency and there are no mechanism for the control parameter's settings, electronic control algorithm, bubble/clot and pressure detection.

Yet another device is disclosed is a European Patent No. EP 2,190,499 B1 dated Mar. 3, 2017: MODULAR DRUG DELIVERY DEVICE FOR ADMINISTERING DISCRETE DOSES OF A MEDICAMENT which relates to the delivery of discrete doses of drugs. The system is attached to the human body and programmed for timings and quantity of dose to be delivered. It facilitates the self-delivery of medicament. The drawbacks of such a device is that that the device cannot be used to withdraw and infuse the blood.

Yet another device is disclosed is U.S. Pat. No. 10,543,306 B2 dated Jan. 8, 2020; APPARATUS FOR MAKING FOR EXTRA CORPOREAL BLOOD CIRCULATION AVAILABLE. The device is used for providing an extracorporeal blood circulation. The blood is taken out continuously from the patient and then processed in the base module and infused again. This is used for faster venting of patient module with priming liquid. However, the device cannot be used to infuse the donor blood.

Therefore, there is a need for a device to perform DVET at a faster and safer rate.

SUMMARY

This summary is provided to introduce a selection of concepts, in a simplified format, that are further described in the detailed description of the invention. This summary is neither intended to identify key or essential inventive concepts of the invention and nor is it intended for determining the scope of the invention.

The present subject matter relates to the Double Volume Exchange Transfusion (DVET) unit for performing blood transfusion in neonates. The DVET unit uses a pump of two syringes to simultaneously draw the infectious blood from the neonates and fresh blood source in one stroke and pumps the fresh blood into the neonate and discharge the infectious blood into the bin.

In an embodiment, a DVET unit is disclosed that comprises a first syringe and a second syringe having a first plunger and a second plunger, respectively, such that the first plunger and the second plunger is adapted to execute a backward stroke and a forward stroke in the respective syringe. The DVET unit also includes a first valve disposed in a housing and in fluid communication with the first syringe, a source of fresh blood, and a specimen. In addition, the DVET unit includes a second valve disposed in the housing and in fluid communication with the second syringe, the specimen, and a waste bin. Further, the first valve is adapted to be closed and the second valve is adapted to be open to draw blood from the source and the specimen into the first syringe and the second syringe, respectively, during the backward stroke. Moreover, the first valve is adapted to be open, and the second valve is adapted to be closed to pump the blood, drawn during the backward stroke, from the first syringe and the second syringe into the specimen and the waste bin, respectively, during the forward stroke.

Another embodiment relates to a method for blood transfusion in a specimen. The method includes receiving, by a controller, an instruction of closing a first valve and opening a second valve, wherein the first valve is in fluid communication with a first syringe, a source of fresh blood, and the specimen, and the second valve is in fluid communication with a second syringe, the specimen, and a waste bin. The method also includes actuating, by the controller, a first plunger inside the first syringe and a second plunger in the second syringe to execute a backward stroke, wherein the blood from the source is drawn into the first syringe and blood from the specimen into the second syringe. In addition, the method includes actuating, by the controller, the first valve in the open state and the second valve in the closed state. Finally, the method includes, actuating, by the controller, the first plunger and the second plunger to execute a forward stroke, wherein the blood from the first syringe is pumped into the specimen and blood from the second syringe is pumped into the waste bin.

According to the present disclosure, the two syringes enables drawing and pumping of the blood from the specimen and fresh blood source and removal of blood into the waste bin in two strokes thereby accelerating the transfusion resulting in less amount of time for the transfusion. Moreover, the actuation of the two valves is synchronous with the forward and backward stroke to efficiently perform the blood transfusion.

To further clarify advantages and features of the present invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 6 illustrates the principal of operation of the device by the help of a flow-chart diagram.

Figure 1:
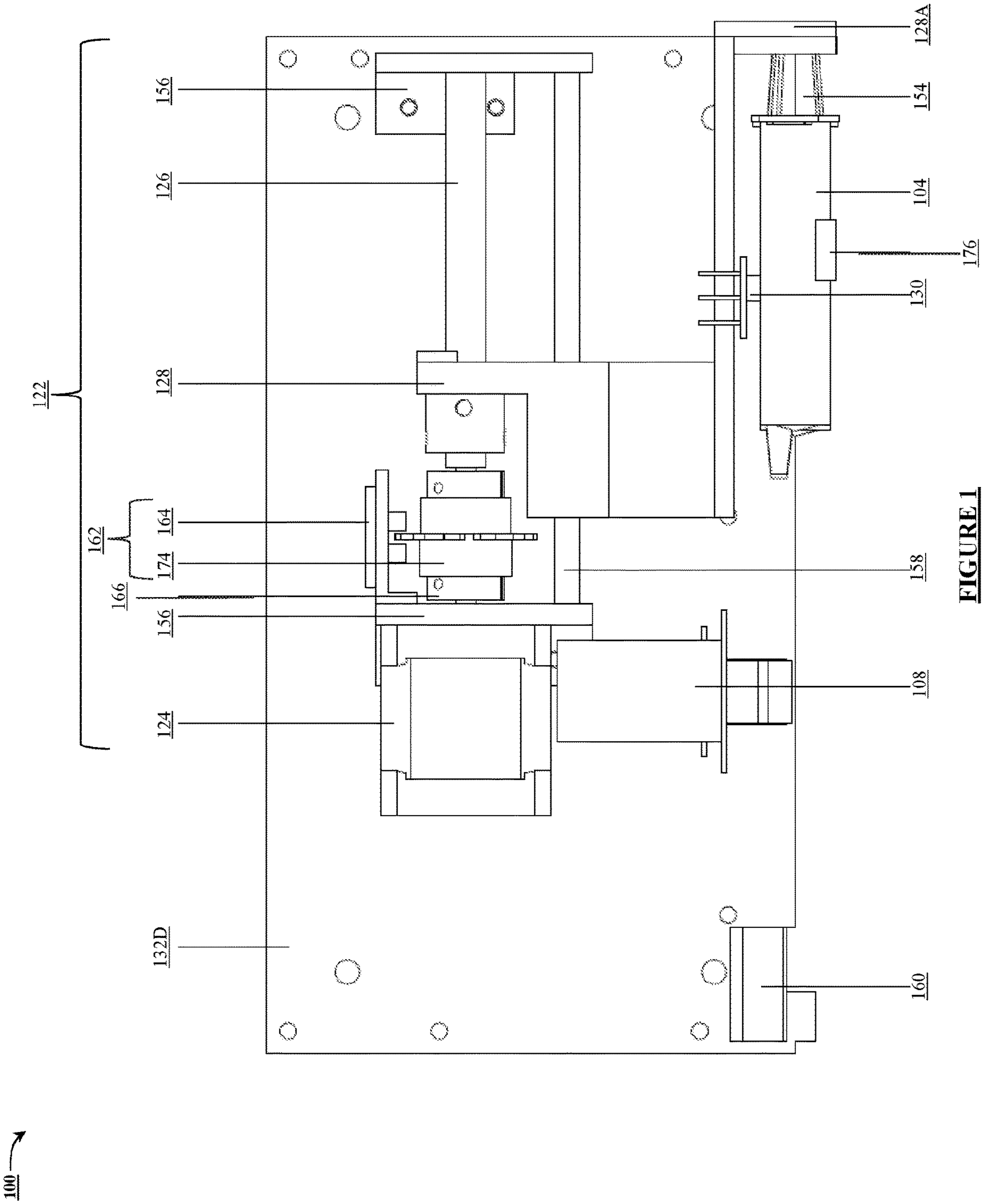
FIG. 1 illustrates the internal assembly showing the structural elements of the device, according to an embodiment of the present disclosure.

Further, skilled artisans will appreciate that elements in the drawings are illustrated for simplicity and may not have necessarily been drawn to scale. Furthermore, in terms of the construction of the device, one or more components of the device may have been represented in the drawings by conventional symbols, and the drawings may show only those specific details that are pertinent to understanding the embodiments of the present invention so as not to obscure the drawings with details that will be readily apparent to those of ordinary skill in the art having benefit of the description herein.

DETAILED DESCRIPTION OF FIGURES

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates. Unless otherwise defined, all technical and scientific terms used herein have the same meaning as commonly understood by one of ordinary skilled in the art to which this invention belongs. The system, methods, and examples provided herein are illustrative only and not intended to be limiting.

For example, the term "some" as used herein may be understood as "none" or "one" or "more than one" or "all." Therefore, the terms "none," "one," "more than one," "more than one, but not all" or "all" would fall under the definition of "some." It should be appreciated by a person skilled in the art that the terminology and structure employed herein is for describing, teaching, and illuminating some embodiments and their specific features and elements and therefore, should not be construed to limit, restrict or reduce the spirit and scope of the present disclosure in any way.

For example, any terms used herein such as, "includes," "comprises," "has," "consists," and similar grammatical variants do not specify an exact limitation or restriction, and certainly do not exclude the possible addition of one or more features or elements, unless otherwise stated. Further, such terms must not be taken to exclude the possible removal of one or more of the listed features and elements, unless otherwise stated, for example, by using the limiting language including, but not limited to, "must comprise" or "needs to include."

Whether or not a certain feature or element was limited to being used only once, it may still be referred to as "one or more features" or "one or more elements" or "at least one feature" or "at least one element." Furthermore, the use of the terms "one or more" or "at least one" feature or element do not preclude there being none of that feature or element, unless otherwise specified by limiting language including, but not limited to, "there needs to be one or more . . . " or "one or more elements is required."

Unless otherwise defined, all terms and especially any technical and/or scientific terms, used herein may be taken to have the same meaning as commonly understood by a person ordinarily skilled in the art.

Reference is made herein to some "embodiments." It should be understood that an embodiment is an example of a possible implementation of any features and/or elements of the present disclosure. Some embodiments have been described for the purpose of explaining one or more of the potential ways in which the specific features and/or elements of the proposed disclosure fulfil the requirements of uniqueness, utility, and non-obviousness.

Use of the phrases and/or terms including, but not limited to, "a first embodiment," "a further embodiment," "an alternate embodiment," "one embodiment," "an embodiment," "multiple embodiments," "some embodiments," "other embodiments," "further embodiment", "furthermore embodiment", "additional embodiment" or other variants thereof do not necessarily refer to the same embodiments. Unless otherwise specified, one or more particular features and/or elements described in connection with one or more embodiments may be found in one embodiment, or may be found in more than one embodiment, or may be found in all embodiments, or may be found in no embodiments. Although one or more features and/or elements may be described herein in the context of only a single embodiment, or in the context of more than one embodiment, or in the context of all embodiments, the features and/or elements may instead be provided separately or in any appropriate combination or not at all. Conversely, any features and/or elements described in the context of separate embodiments may alternatively be realized as existing together in the context of a single embodiment.

Any particular and all details set forth herein are used in the context of some embodiments and therefore should not necessarily be taken as limiting factors to the proposed disclosure.

Embodiments of the present invention will be described below in detail with reference to the accompanying drawings.

Figure 2:
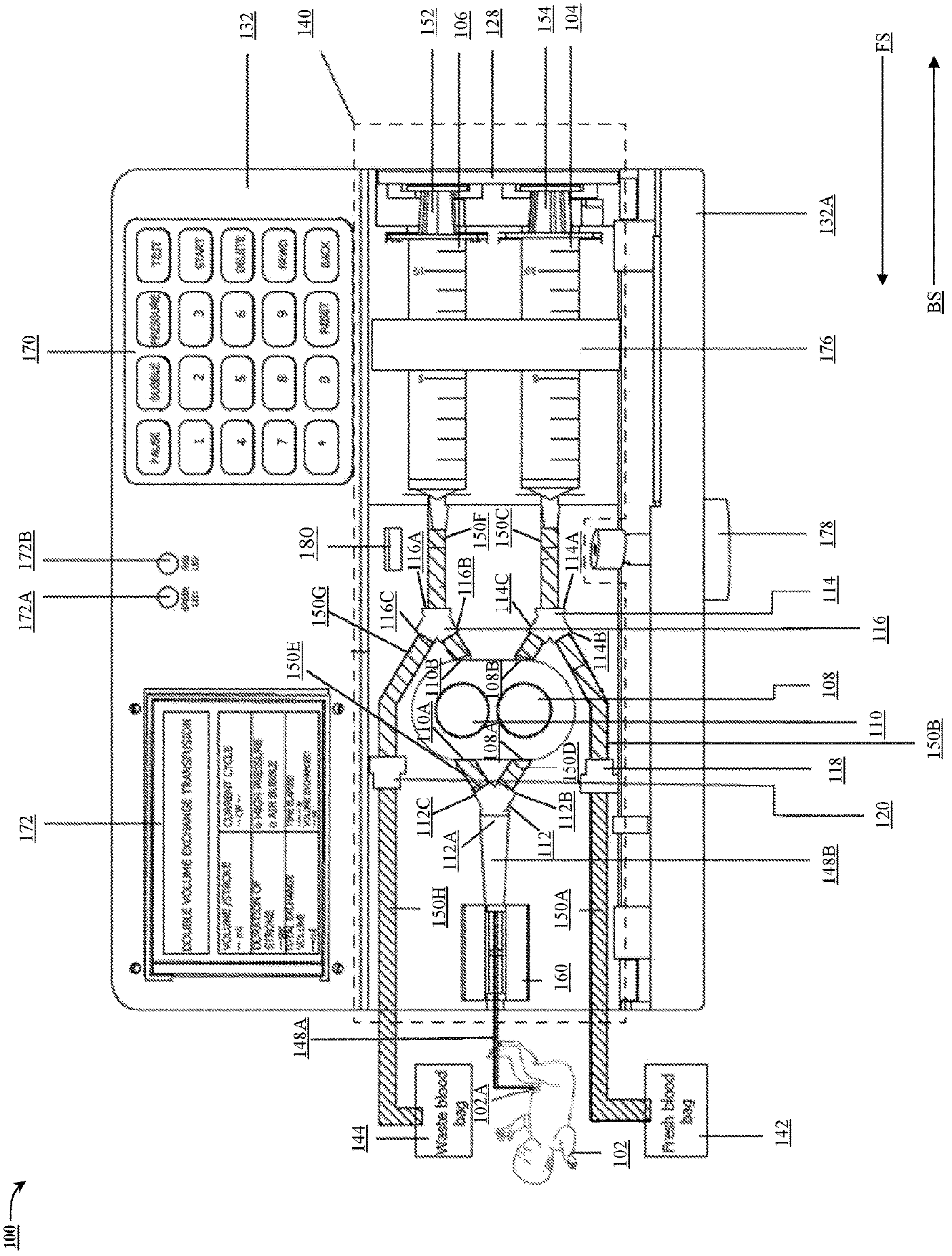
FIG. 2 shows the front view of the device, according to an embodiment of the present disclosure.
Figure 3:
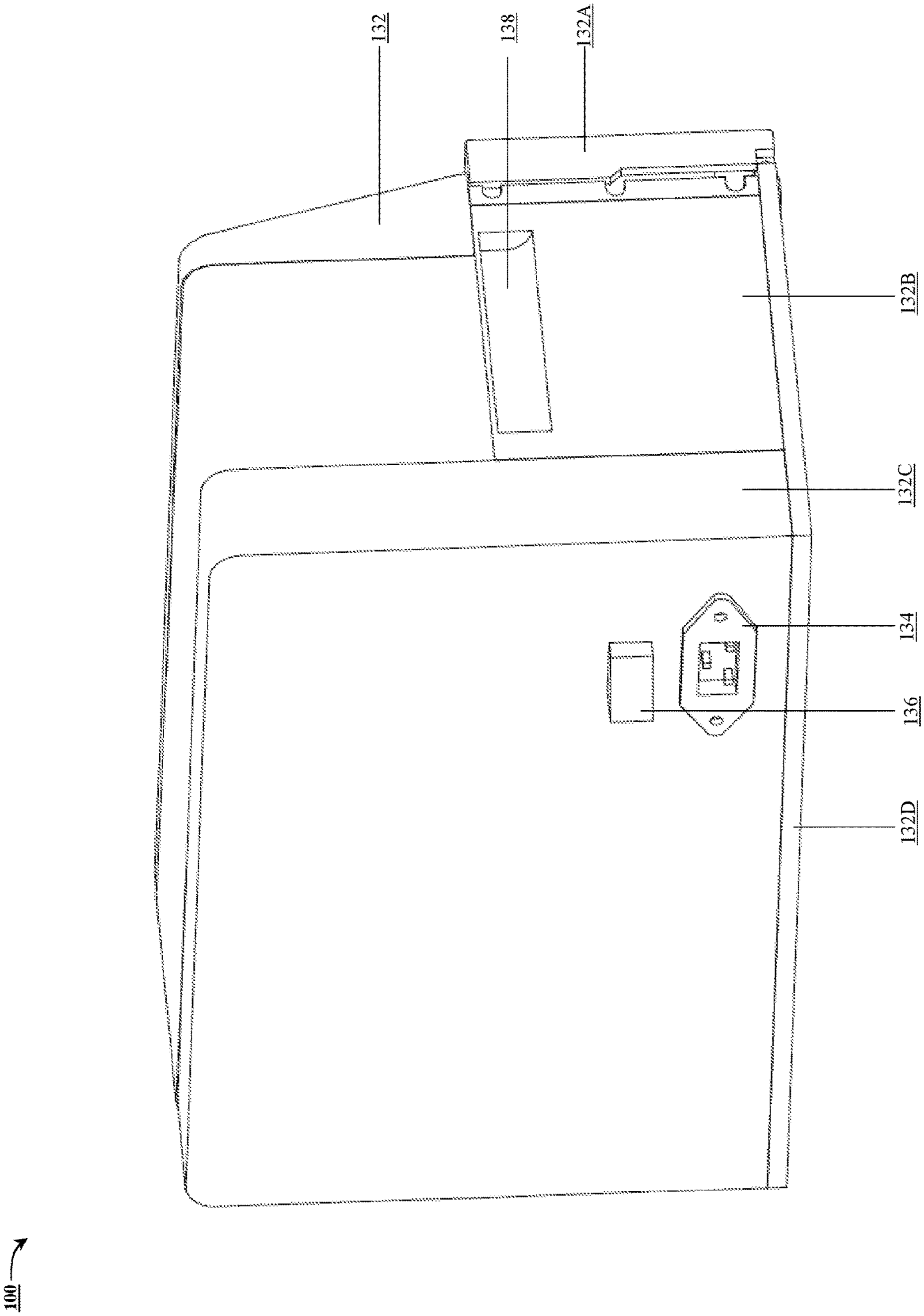
FIG. 3 shows the back-side structural view of the device, according to an embodiment of the present disclosure.

FIGS. 1 to 3 illustrates various views of a Double Volume Exchange Transfusion (DVET) unit 100, according to an embodiment of the present disclosure. Specifically, FIG. 1 shows a top view of the DVET unit 100 showing the internal components of the DVET unit 100 while FIG. 2 shows a front view of the DVET unit 100. Further, FIG. 3 shows the back-side structural view of the device. The DVET unit 100 may be used to perform blood transfusion in specimen 102, such as a neonate. The DVET unit 100 is designed to quickly transfuse the fresh blood in the specimen 102. Moreover, the DVET unit 100 is designed to discharge the blood from the specimen 102 into a waste bin 144. The DVET unit 100 employs a dual syringe pump that simultaneously draws the blood from the neonate and a fresh blood source 142 in one stroke. Further, the dual syringe pumps the drawn blood from the fresh blood source 142 into the neonate and discharge the blood from the neonate to a waste bin 144. Accordingly, the DVET unit 100 transfuses a unit of the blood in the neonate in one cycle as compared to conventional devices that performs the same operation in two cycles. As a result, the DVET unit 100 is two times quicker than the conventional devices.

The DVET unit 100 may include, but is not limited to, a first syringe 104, a second syringe 106, a first valve 108, a second valve 110, a first Y-connector 112, second Y-connector 114, a third Y-connector 116, a first one-way valve 118, a second one-way valve 120, an actuation unit 122, a stepper motor 124, a screw 126, a carriage 128, a push button 130.

The components of the DVET unit 100 may be installed in a housing 132 of the DVET unit 100. The housing may have a transparent front cover 132A, side covers 132B, and a back cover 132C. Further, the front cover 132A, the side covers 132B, and the back cover 132C may be installed at a base plate 132D of the housing 132. The front cover 132A may be removed by unlocking a lock 178 by inserting a key in a key slot 180. The housing 132 may include a socket 134 on the back cover 132C to supply power to the DVET unit 100. In addition, the housing 132 may include an ON/OFF switch 136 on the back cover 132C. Although not shown, the housing 132 may also house a power converter that covers the AC power supply to DC supply to power various aforementioned components of the DVET unit 100. The housing 132 may also include a handle 138 to hold and carry the DVET unit 100.

In one example, the first syringe 104, the second syringe 106, the first valve 108, the second valve 110, the first Y-connector 112, second Y-connector 114, the third Y-connector 116, the first one-way valve 118, the second one-way valve 120 may define a blood circuit 140.

The blood circuit 140 may include different sub-circuits for the blood circuit 140. One of the sub-circuits, referred to as a first sub-circuit, enables the blood to flow from a fresh blood source 142 to the neonate 102. The first sub-circuit includes the first one-way valve 118, the first syringe 104, the first valve 108, the first Y-connector 112. The constitution of the first sub-circuit includes fluidic coupling of the aforementioned components. In one example, the first Y-connector 112 has a first port 112A adapted to fluidically couple to the specimen 102. Further, the first Y-connector 112 has a second port 112B adapted to fluidically couple with an inlet port 108A of the first valve 108 and a third port 112C adapted to fluidically couple an inlet port 110A of the second valve 110. Accordingly, the first Y-connector 112 fluidically couples the specimen 102 to inlet ports of each of the first valve 108 and the second valve 110. On the other hand, the second Y-connector 114 has a first port 114A that fluidically couples with the first syringe 104 and a second port 114B that fluidically couples to the fresh blood source 142 via the first one-way valve 118. The second Y-connector 114 has a third port 114C that fluidically couples with an outlet port 108B of the first valve 108. Accordingly, the second Y-connector 114 fluidically couples the first syringe 104 with an outlet port of the first valve 108 and the source.

Another sub-circuit may be termed as the second sub-circuit that includes the first Y-connector 112, the second valve 110, the third Y-connector 116, the second syringe 106, and the second one-way valve 120. The constitution of the second sub-circuit includes fluidic coupling of the aforementioned components. In one example, the third Y-connector 116 has a first port 116A that fluidically couples with the second syringe 106 and a second port 116B that fluidically couples with an outlet port 110B of the second valve 110. The third Y-connector 116 has a third port 116C that fluidically couples to the waste bin 144 via the second one-way valve 120. Accordingly, the third Y-connector 116 adapted to fluidically couple the second syringe 106 with an outlet port of the second valve 110 and the waste bin 144. In one example, the blood circuit 140 may include different hoses, pipes, and adaptors that couple the aforementioned components of the blood circuit 140. For instance, the blood circuit 140 may have an umbilical catheter 148A that couples an umbilical vein 102A of the specimen 102 via a tapered adapter 148B to the first port 112A of the first Y-connector 112.

In addition, the DVET unit 100 includes tubes 150A-H. In addition, a tube 150A couples the fresh blood source 142 to the first one-way valve 118 while a tube 150B couples the first one-way valve 118 to the second port 114B. Further, another tube 150C couples the first port 114A to the first syringe 104. Yet another tube 150D couples the inlet port 108A to the second port 112B while a tube 150E couples the inlet port 110A to the third port 112C. A tube 150F couples the first port 116A to the second syringe 106 while another tube 150G couples the third port 116C to the one-way valve. Finally, a tube 150H couples the one-way valve to the waste bin 144. In one example, the tubes 150A-H allows an airtight coupling thereby reducing the instance of cavitation in the blood circuit 140.

In one example, the blood flows through the blood circuit 140 upon actuation of the first syringe 104 and the second syringe 106. Accordingly, the first syringe 104 may include a first plunger 154 and the second syringe 106 may include a second plunger 152. Further, each of the first plunger 154 and the second plunger 152 can displace inside the first syringe 104 and the second syringe 106 respectively to execute a backward stroke and a forward stroke in the respective syringe. Referring now to FIG. 2, the backward stroke is designated by arrow BS while the forward stroke is denoted by arrow FS.

Referring to FIG. 1, the actuation unit 122 is adapted to actuate the first plunger 154. The actuation unit 122 may be adapted to secure the first syringe 104 and the second syringe 106 thereto and may actuate the first plunger 154 and the second plunger 152 to execute the forward stroke and the backward stroke. The actuation unit 122 may include the stepper motor 124 and a screw 126 coupled to the stepper motor 124 and adapted to rotate clockwise and anticlockwise by the stepper motor 124. The actuation unit 122 also includes the carriage 128 that is mounted on the screw 126 and is adapted to move linearly along a length of the screw 126 in response to the rotation of the screw 126. The carriage 128 has a movement link 128A that couples to the first plunger 154 and the second plunger 152. The carriage 128 may move on the principle of the screw 126 jack mechanism. Further, the carriage 128 is coupled to the first plunger 154 and the second plunger 152. Accordingly, the movement of the carriage 128 causes either the backward stroke or the forward stroke depending on the direction of motion. Further, the carriage 128 synchronizes the backward stroke and the forward stroke of the first plunger 154 and the second plunger 152 so that the first plunger 154 and the second plunger 152 draws/pump an equal volume of blood in the first syringe 104 and the second syringe 106. The actuation unit 122 may also include a pair of columns 156 to secure the screw 126 to the base plate 132D. In addition, the actuation unit 122 includes a guide rail 158 to guide the sliding of the carriage 128. The actuation unit 122 may also include a pressure pad 176 that secures the first syringe 104 and the second syringe 106 to the housing 132.

According to the present disclosure, the DVET unit 100 may include various safety measures that ensure a safe blood transfusion process. In one example, the DVET unit 100 may include a sensor 160 attached to umbilical catheter 148A connecting the specimen 102 and the first Y-connector 112. The sensor 160 is an infrared sensor that is adapted to detect bubbles and clots in the blood passing through the umbilical catheter 148A. The signal from the sensor 160 may inhibit the backward stroke or the forward stroke of the first plunger 154 and the second plunger 152.

In addition to the sensor 160, the DVET unit 100 may include a pressure detection unit 162 adapted to detect pressure gradient in the umbilical catheter 148A, wherein the pressure gradient is based on resistance in the backward stroke and the forward stroke by the actuation unit 122. The pressure detection unit 162 may include an infrared emitter and receiver 164 and a disk 174 mounted on a coupling 166 which couples the stepper motor 124 to the screw 126. The disk 174 has fins that rotates between the emitter and the receiver and are adapted to impede the transmission of the emitter and the receiver. Accordingly, the pressure sensor 162 generates a pulse every time the fins does not impede the transmission and the number of generated pulses per unit time indicates the rotational speed of the screw 126. During the normal operation, the pressure sensor 162 generates the pulses at a predetermined rate. However, change of the pressure in scenarios such as, a blood clot or air leakages anywhere in the blood circuit 140, may either resist or ease the backward stroke or forward stroke of the first plunger 154 and the second plunger 152. The resistance and the ease in the stroke causes the change in the rate of displacement of the carriage 128 and consequently, the rotational speed of the screw 126. The change in the rotational speed varies the generated pulse per unit time. In one example, a case of change in the generated pulses per unit time greater than a threshold is interpreted as the occurrence of one of the aforementioned scenarios and accordingly, the operation of the stepper motor 124 may be stopped. The actuation unit 122 may also include a push button 130 that indicates the mounting of either the first syringe 104 and or the second syringe 106 or both on the carriage 128.

In one example, the DVET unit 100 may include an input/output interface that provides information to an operator regarding the operation of the DVET unit 100. For instance, the DVET unit 100 may include a keypad 170 that allows the operator to insert the operation parameters for the DVET unit 100, such as, volume per stroke, Duration of Stroke, baby weight, Total Exchange volume etc., start/stop/pause/reset the DVET unit 100, among other examples. The DVET unit 100 also includes a display 172 that indicates the value of set parameters and instantaneous value of different parameters. The DVET unit 100 may include a green light 172A indicating normal operation and a red light 172B indicating an error in the operation of the DVET unit 100.

Figure 4:
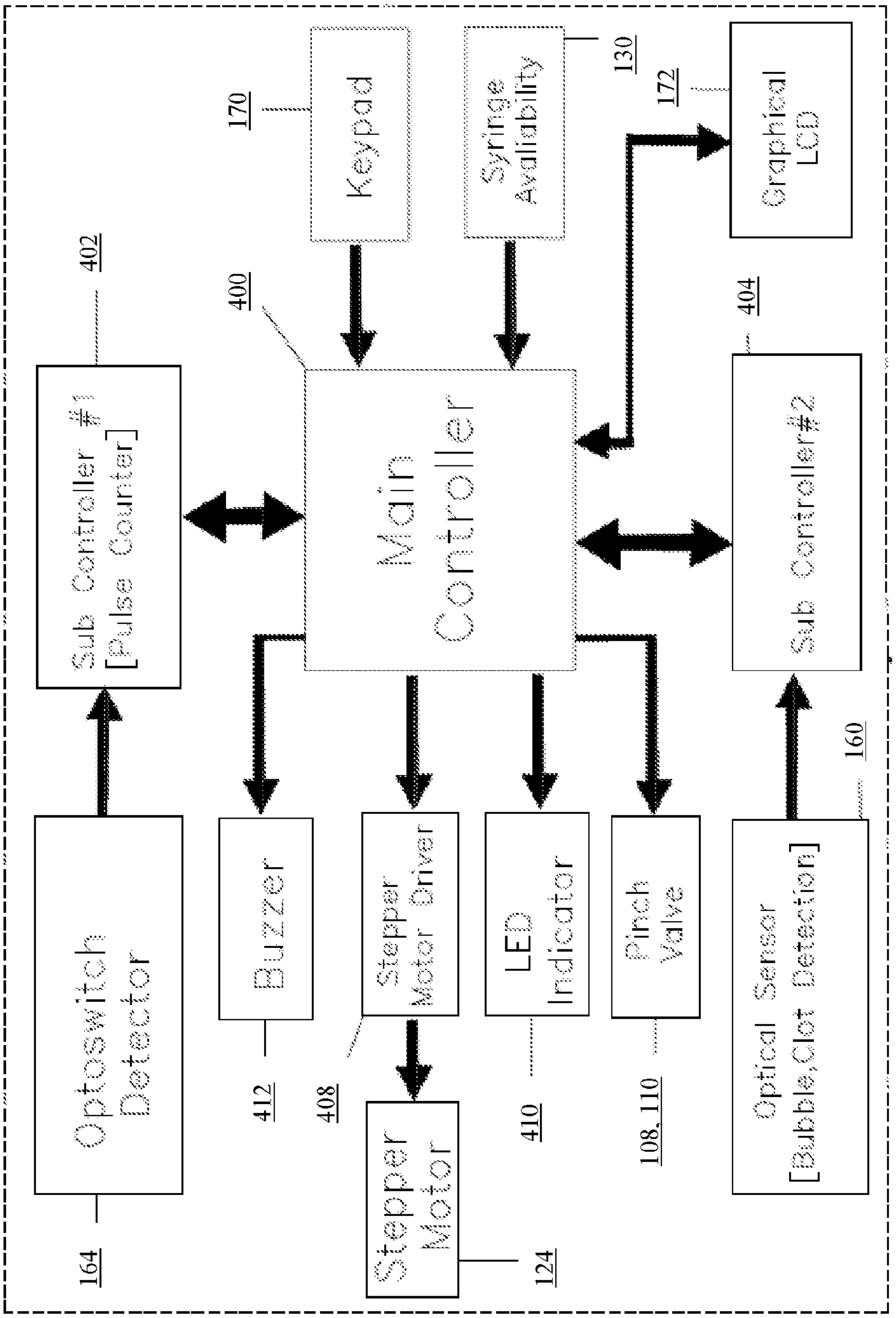
FIG. 4 shows the electronic building block of the device, according to an embodiment of the present disclosure.

Referring now to FIG. 4 that illustrates a controller 400, according to an embodiment of the present disclosure. The controller 400 is the brain of the DVET unit 100 and is coupled to the sensors and the actuation unit 122, the first valve 108, and the second valve 110 to perform the blood transfusion. In an embodiment, the controller 400 may include, but is not limited to, a processor, memory, modules. The modules and the memory may be coupled to the processor. The processor can be a single processing unit or several units, all of which could include multiple computing units. The processor may be implemented as one or more microprocessors, microcomputers, microcontrollers, digital signal processors, central processing units, state machines, logic circuitries, and/or any devices that manipulate signals based on operational instructions. Among other capabilities, the processor is configured to fetch and execute computer-readable instructions and data stored in the memory.

The memory may include any non-transitory computer-readable medium known in the art including, for example, volatile memory, such as static random access memory (SRAM) and dynamic random access memory (DRAM), and/or non-volatile memory, such as read-only memory (ROM), erasable programmable ROM, flash memories, hard disks, optical disks, and magnetic tapes.

The modules, amongst other things, include routines, programs, objects, components, data structures, etc., which perform particular tasks or implement data types. The modules may also be implemented as, signal processor(s), state machine(s), logic circuitries, and/or any other device or component that manipulate signals based on operational instructions.

Further, the modules can be implemented in hardware, instructions executed by a processing unit, or by a combination thereof. The processing unit can comprise a computer, a processor, such as the processor, a state machine, a logic array, or any other suitable devices capable of processing instructions. The processing unit can be a general-purpose processor which executes instructions to cause the general-purpose processor to perform the required tasks or, the processing unit can be dedicated to performing the required functions. In another embodiment of the present disclosure, the modules may be machine-readable instructions (software) which, when executed by a processor/processing unit, perform any of the described functionalities. Further, the data serves, amongst other things, as a repository for storing data processed, received, and generated by one or more of the modules.

The controller 400 may interact with the push button 130 to determine the availability of the syringes. The controller 400 may also interact with the keypad 170 to receive the input parameters. The controller 400 may receive the signal from the pressure sensor 162 and the sensor 160 and via their respective sub-controller 402 and 404 respectively. The controller 400 may process the received inputs and may operate various components. For instance, the controller 400 may operate the first valve 108 and the second valve 110. In addition, the controller 400 may operate the stepper motor 124 via a stepper motor driver 408. Moreover, the controller 400 may provide operate the indicators via the LED indicator 410. Finally, the controller 400 may provide aural feedback via a buzzer 412.

Figure 5:
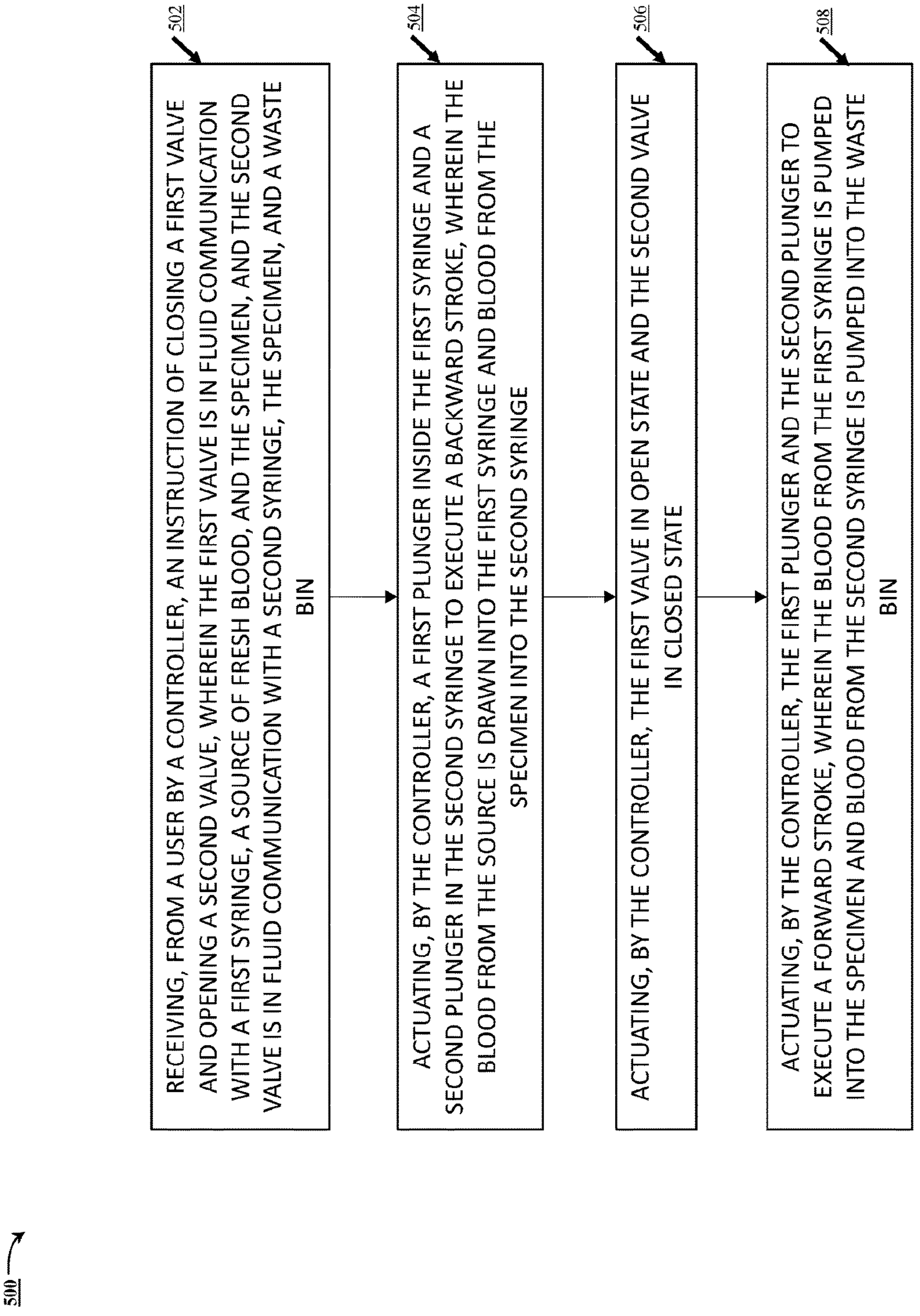
FIG. 5 illustrates a method for blood transfusion, according to an embodiment of the present disclosure.

The operation of the DVET unit 100 will now be explained with respect to FIG. 5 which illustrates a method 500 for blood transfusion. The order in which the method steps are described below is not intended to be construed as a limitation, and any number of the described method steps can be combined in any appropriate order to execute the method or an alternative method. Additionally, individual steps may be deleted from the method without departing from the spirit and scope of the subject matter described herein.

The method 500 can be performed by programmed computing devices, for example, based on instructions retrieved from non-transitory computer readable media. The computer readable media can include machine-executable or computer-executable instructions to perform all or portions of the described method. The computer readable media may be, for example, digital memories, magnetic storage media, such as a magnetic disks and magnetic tapes, hard drives, or optically readable data storage media.

In one example, the method 500 can be performed partially or completely by the DVET unit. The method 500 begins at step 502, at which an instruction to initiate the blood transfusion process. In one example, the instruction may include closing the first valve 108 and opening the second valve 110. Thereafter, at step 504, the controller 400 may actuate the first plunger 154 inside the first syringe 104 and the second plunger 152 in the second syringe 106 to execute the backward stroke, such that the blood from the fresh blood source 142 is 20 drawn into the first syringe 104 and blood from the specimen 102 into the second syringe 106. In one example, the blood from the fresh blood source 142 flows a fluid path that includes the tube 150A, the first one-way valve 118, the second port 114B of the second Y-connector 114, the first port 114A of the second Y-connector 114, and the first syringe 104. Simultaneously, the blood from the specimen 102 is drawn into the second syringe 106 via a fluid path that includes, the umbilical catheter 148A, the tapered adapter 148B, the first port 112A of the first Y-connector 112, inlet port 110A of the second valve 110, the outlet port 110B of the second valve 110, the first port 116A of the third connector, and the tube.

Further, at step 506, the controller 400 may actuate the first valve 108 in the open state and the second valve 110 in the closed state. Thereafter, at step 508, the controller 400 may actuate the first plunger 154 and the second plunger 152 to execute the forward stroke, such that the blood from the first syringe 104 is pumped into the specimen 102 and blood from the second syringe 106 is pumped into the waste bin 144. In one example, the blood in the first syringe 104 flows into the specimen 102 via a fluid path that includes tube 150C, the first port 114A of the second Y-connector 114, the third port 114C of the second Y-connector 114, the first valve 108, and the tube 150D.

FIG. 6 provides a detailed methodology 600 regarding the operation of the DVET unit 100. The methodology 600 includes confirming if the adapter is plugged into the power socket 134. Thereafter, mounting of the first syringe 104 or the second syringe 106 is detected. In case the mounting of the first syringe 104 and the second syringe 106 is detected, the pressing of the "*" key on the keypad 170. In case the "*" key is detected, the "RESET" key is pressed to reset all previously fed parameters. Thereafter, the parameters are inserted, such as volume/stroke, duration of a stroke, and total exchange volume. Thereafter, the parameters are checked. In case the parameters are incorrect, the parameter is re-entered using the keypad 170. On the other hand, in case the parameters are correct, the total number of cycles is calculated as:

Calculate Total Number of Cycle=Total Exchange volume/Volume per stroke

Thereafter, the total step count is calculated for the stepper motor 124 for clockwise movement is determined. Once determined, receipt of "START" command is checked, if the command is received, a red light is turned ON to indicate the beginning of the process and thereafter, the first valve 108 is closed and the second valve 110 is opened. Once the valves are operated, the total step for the clockwise rotation is determined and the stepper motor 124 is rotated in the clockwise direction to cause backward stroke resulting in drawing the blood from the specimen 102 to the second syringe 106 and from the fresh blood source 142 to the first syringe 104. During the backward stroke, receipt of "PAUSE" command is checked. In case no such command is received if an air bubble/clot is detected. In case of no such detection, the pressure variation is checked. In case the pressure variation is not detected, the stepper motor 124 continues to actuate the plungers to perform the backward stroke. On the other hand, if any of the PAUSE commands, bubble/air detection, or pressure variation is detected, the stepper motor 124 is stopped, and a buzzer 412 is sounded.

Towards the end of the backward stroke, if step count is now equal to the total step count. In case the step count is equal to the total step count, the stepper motor 124 is stopped and a delay of 5 seconds is executed. Thereafter, the first valve 108 is closed and the second valve 110 is opened and the total step for anti-clockwise rotation is determined. Thereafter, the stepper motor 124 is rotated in anti-clockwise direction to cause the first plunger 154 and the second plunger 152 forward stroke. During the forward stroke, the blood from the first syringe 104 flows into the specimen 102 while the blood in the second syringe 106 flows into the waste bin 144. During the forward stroke, receipt of the signal of any of the "PAUSE" command, bubble/clot detection, pressure variation is checked and receipt of any of such signals forfeit the rotation of the stepper motor 124. Upon completion of the forward stroke, the processes are of clockwise rotation followed by anti-clockwise rotation are repeated until the total volume of blood is transfused. Once the volume is transfused, the operation is completed, and the buzzer is sounded to indicate the completion of the process.

According to the present disclosure, the DVET unit 100 was subjected a series of following tests:

EXAMPLE 1

Three beakers were placed, where one beaker represented "Fresh blood bank bag" filled with red colored solution of 200 ml containing 10% glycerol, water and red dye, to simulate human blood; the second beaker represented "Waste blood bag", which was empty to begin with and third one represented "Patient body" filled with 200 ml of solution containing 10% glycerol and water. All the tubings and valves were placed in their proper position in the blood flow circuit. An umbilical catheter 148A was placed with the distal end in the "Patient body" beaker and proximal end connected to the stem of the Y-shaped part of the tubing assembly: one blood transfusion tubing set connected the "Fresh blood bank bag" beaker to the tubing assembly; one blood transfusion tubing set connected the tubing assembly to "Waste blood bag" beaker.

The ON/OFF switch was moved to ON position and the user defined parameters were set as follows:

Volumes/Stroke: –10 ml

Duration of stroke: –60 seconds

Total exchanged volume: –200 ml

System Calculated parameters as shown below

Total number of cycles: –20

After setting of input parameters, "START" key was pressed to start the process. After the process was completed, it was observed that the empty beaker i.e. "Waste blood bag" had filled up with the 200 ml red colour liquid solution, "Fresh blood bag" beaker was empty and "Patient body" beaker was filled up with another 200 ml of red colour liquid solution. The concentration of the liquid solution present in the "Patient body" beaker was very close to the solution that was present in the "Fresh blood bank bag" beaker before starting the process.

EXAMPLE 2

Starting with the Example 1 above, the experiment was performed again, where red colored solution was replaced with human blood in a blood bank bag issued by the blood bank; and the rest of the arrangement was same as stated above. Before the experiment, basic hematological and biochemical parameters were measured in the fresh blood. After the process completion, these blood parameters were again measured and found to be similar in range with the initial values.

EXAMPLE 3

Starting with the Example 1 above, air bubbles were artificially introduced in the tubings using the needle and syringe arrangement and process was started. It was observed that when the air bubble passed through the Air bubble/clot detector unit, system generates the alarm by continuous blinking of the Red LED indicator and the process stopped. After human intervention to remove the bubble from the tubings and placing them in the proper position in the blood flow circuit and on pressing the "BUBBLE" key, the DVET unit 100 resumed its operation from where it was stopped.

EXAMPLE 4

Starting with the Example 1 above, clotted blood was artificially introduced in the tubings and process was started. It was observed that when the clot passed through the Air bubble/clot detector unit, the DVET unit 100 generated an alarm by continuous blinking of the Red LED indicator and the process stopped. After human intervention to remove the clots from the tubings and placing them in the proper position in the blood flow circuit and on pressing the "BUBBLE" key, the DVET unit 100 resumed its operation from where it was stopped.

EXAMPLE 5

Starting with the Example 1 above, the pressure difference in the tubings was artificially generated by kinking the catheter tube during the process. It was observed that after a little while, the DVET unit 100 generates the alarm by continuous blinking of the Red LED indicator and the process stopped. After human intervention to smoothen the kinked tubing and placing them in the proper position in the blood flow circuit and pressing the "PRESSURE" key, the DVET unit 100 resumes its operation from where it was stopped.

EXAMPLE 6

When all the activities stated in the above Example 1, Example 3, Example 4 and Example 5 were integrated and the DVET unit 100 was operated, it was observed that they were carried out satisfactorily.

According to the present disclosure, there are various advantages of the DVET unit 100. The main advantage of the DVET unit 100 is that it eliminates the manual process of double volume exchange transfusion in neonates, which is laborious, tedious, repetitive and prone to error. Yet another advantage of the DVET unit 100 is that it prevents human errors during the process, and requires minimum human intervention. Yet another advantage of the DVET unit 100 is that it always provides a well calibrated and smooth inflow and outflow of the blood into patient, to ensure no hemolysis. Yet another advantage of this DVET unit 100 is electronically controlled dual (forward and backward) movement of the syringe pumps, until the end of the process for blood withdrawal and infusion.

Yet another advantage of the DVET unit 100 is that it uses LCD as GUI for display of user defined and calculated parameters, keypad for user interfaces and control. Yet another advantage of the DVET unit 100 is that it has sensors and detectors for air-bubble/clot and change of pressure in tubings and catheter, which send a signal to generate alarm and pause the device. Yet another advantage of the DVET unit 100 is that after the error is resolved by human intervention (such as removal of air bubble, clot, kink, leakage), the device can be started again from the same position, where it was paused during error. Yet another advantage of the DVET unit 100 is the use of micro stepping action of stepper motor 124, which minimizes stepping error while reciprocating the motion. So, a perfect conversion of circular to linear motion is there. Yet another advantage of the DVET unit 100 is the use of LEDs and alarms to indicate different status of the DVET unit 100, during the DVET. Yet another advantage of the DVET unit 100 is the use of audio-visual alarms to indicate different status of the DVET unit 100, during the DVET. Yet another advantage of the DVET unit 100 is simple mechanisms and the use of light weight material for minimum self-weight. Yet another advantage of the DVET unit 100 is the use of electronic controllers-based circuitry for precisely control movement of syringe pump, and overall synchronization of each and every component. Yet another advantage of the DVET unit 100 is that all the tubes, catheter along with one-way valves are disposable. Yet another advantage of this DVET unit 100 is the simple operating method, which reduces the requirement of cumbersome training of the users. Yet another advantage of this the DVET unit 100 is that it is equipped with a re-chargeable battery connected with main power line for uninterrupted operation during power cut.

While specific language has been used to describe the present disclosure, any limitations arising on account thereto, are not intended. As would be apparent to a person in the art, various working modifications may be made to the method in order to implement the inventive concept as taught herein. The drawings and the foregoing description give examples of embodiments. Those skilled in the art will appreciate that one or more of the described elements may well be combined into a single functional element. Alternatively, certain elements may be split into multiple functional elements. Elements from one embodiment be to may added another embodiment.

We claim:

1. A Double Volume Exchange Transfusion (DVET) unit comprising:

a first syringe and a second syringe having a first plunger and a second plunger, respectively, wherein each of the first plunger and the second plunger is adapted to execute a backward stroke and a forward stroke in the respective syringe;

a first valve disposed in a housing and in fluid communication with the first syringe, a fresh blood source, and a specimen;

a second valve disposed in the housing and in fluid communication with the second syringe, the specimen, and a waste bin, and a controller adapted to:

actuate the first valve to close and the second valve to open during the backward stroke; and actuate the first valve to open and the second valve to close during the forward stroke;

wherein the first valve is adapted to be closed and the second valve is adapted to be open to draw blood from the fresh blood source and the specimen into the first syringe and the second syringe, respectively, during the backward stroke, and the first valve is adapted to be open and the second valve is adapted to be closed to pump the blood, drawn during the backward stroke, from the first syringe and the second syringe into the specimen and the waste bin, respectively, during the forward stroke.

2. The DVET unit as claimed in claim 1, comprising:

a first Y-connector adapted to fluidically couple the specimen to inlet ports of each of the first valve and the second valve;

a second Y-connector adapted to fluidically couple the first syringe with an outlet port of the first valve and the fresh blood source; and a third Y-connector adapted to fluidically couple the second syringe with an outlet port of the second valve and the waste bin.

3. The DVET unit as claimed in claim 1, comprising:

a first one-way valve adapted to prevent backflow from the first syringe to the fresh blood source; and a second one-way valve adapted to prevent backflow from the waste bin to the second syringe.

4. The DVET unit as claimed in claim 1, comprising an actuation unit coupled to the first plunger and the second plunger to execute the backward stroke and the forward stroke.

5. The DVET unit as claimed in claim 4, wherein the actuation unit comprising:

a stepper motor;

a screw coupled to the stepper motor and adapted to rotate clockwise and anticlockwise by the stepper motor;

a carriage mounted on the screw and coupled to ends of the first plunger and the second plunger, wherein the carriage moves along a length of the screw in response to the rotation of the screw.

6. The DVET unit as claimed in claim 5, comprising a push button adapted to indicate the mounting of one of the first syringe and the second syringe on the carriage.

7. The DVET unit as claimed in claim 1, comprising a sensor coupled to the controller and attached to a hose connecting the specimen and the first Y-connector, and adapted to detect a bubble or a clot in the blood passing through the hose, wherein the controller is configured to pause one of the backward stroke and the forward stroke in the presence of the sensed bubble or clot in the blood.

8. The DVET unit as claimed in claim 7, comprising a pressure sensor adapted to detect pressure gradient in the hose, wherein the pressure gradient is based on one of a resistance and ease in the backward stroke and the forward stroke by the actuation unit.

9. A method for blood transfusion in a specimen, the method comprising:

obtaining the DVET unit according to claim 1;

receiving, from a user by the controller, an instruction of closing the first valve and opening the second valve, wherein the first valve is in fluid communication with the first syringe, a source of fresh blood, and the specimen, and the second valve is in fluid communication with the second syringe, the specimen, and a waste bin;

actuating, by the controller, the first plunger inside the first syringe and the second plunger in the second syringe to execute a backward stroke, wherein the blood from the source of fresh blood is drawn into the first syringe and blood from the specimen into the second syringe;

actuating, by the controller, the first valve in open state and the second valve in closed state;

actuating, by the controller, the first plunger and the second plunger to execute a forward stroke, wherein the blood from the first syringe is pumped into the specimen and blood from the second syringe is pumped into the waste bin.

* * * * *